(12) United States Patent
Appelman et al.

(10) Patent No.: US 8,956,520 B2
(45) Date of Patent: Feb. 17, 2015

(54) ELECTROCHEMICAL PROCESS TO PREPARE CHEMICALS USING A CYANIDE SALT

(75) Inventors: Wilhelmus Joannes Theodorus Maria Appelman, Melick (NL); Hans Lammers, Arnhem (NL); Arie Volmer, Gulpen (NL); Tjerk Oedse Boonstra, Duiven (NL); Adrianus Maria Reichwein, Velp (NL)

(73) Assignee: Akzo Nobel Chemicals International B.V., Amersfoort (NL)

(*) Notice: Subject to any disclaimer, the term of this patent is extended or adjusted under 35 U.S.C. 154(b) by 564 days.

(21) Appl. No.: 13/322,702

(22) PCT Filed: Jun. 3, 2010

(86) PCT No.: PCT/EP2010/057788
§ 371 (c)(1),
(2), (4) Date: Feb. 9, 2012

(87) PCT Pub. No.: WO2010/139763
PCT Pub. Date: Dec. 9, 2010

(65) Prior Publication Data
US 2012/0132536 A1  May 31, 2012

Related U.S. Application Data

(60) Provisional application No. 61/223,189, filed on Jul. 6, 2009.

(30) Foreign Application Priority Data

Jun. 5, 2009 (EP) ..................................... 09162119

(51) Int. Cl.
*B01D 61/44* (2006.01)
*C07C 227/18* (2006.01)

(52) U.S. Cl.
CPC .............. *C07C 227/18* (2013.01); *B01D 61/44* (2013.01)
USPC ............................ 204/531; 204/534; 204/537

(58) Field of Classification Search
USPC ........................................ 204/531, 534, 537
See application file for complete search history.

(56) References Cited

U.S. PATENT DOCUMENTS 2,855,428 A    10/1958   Singer et al.
3,061,628 A *  10/1962   Singer, Jr. et al. ............ 558/346

(Continued)

FOREIGN PATENT DOCUMENTS

CA      1067451         12/1979
DE      4211713 A1      10/1993

(Continued)

OTHER PUBLICATIONS

English language machine translation of Office Action dated Jun. 11, 2013 for corresponding Japanese Patent Application No. 2012-513628.
English language machine translation of JP 7-258878 A published Oct. 9, 1995.

(Continued)

*Primary Examiner* — Arun S Phasge
(74) *Attorney, Agent, or Firm* — Sandra B. Weiss

(57) ABSTRACT

The present invention relates to a process comprising the reaction of a cyanide with a hydrogen cyanide-reactive compound, characterized in that the cyanide is a cyanide salt and the process is an electrochemical process involving the transporting of a reaction mixture to which cyanide salt has been added through an electrochemical cell, in which process the cyanide salt reacts with the hydrogen cyanide-reactive compound while at least partly under the influence of an electric current the cyanide salt is acidified and the salt cation content is reduced.

18 Claims, 5 Drawing Sheets

(56) References Cited

U.S. PATENT DOCUMENTS

| | | | |
|---|---|---|---|
| 4,024,033 A | 5/1977 | Alfenaar et al. | |
| 4,743,603 A | 5/1988 | Bulot | |
| 5,225,054 A * | 7/1993 | Boateng | 204/520 |

FOREIGN PATENT DOCUMENTS

| | | |
|---|---|---|
| EP | 0 124 007 A2 | 7/1984 |
| EP | 0 237 239 A2 | 9/1987 |
| EP | 1004571 | 5/2000 |
| FR | 2230588 A1 | 12/1974 |
| JP | 50-32095 | 3/1975 |
| JP | 60-36682 A | 2/1985 |
| JP | 60-136559 | 7/1985 |
| JP | 62-223193 A | 10/1987 |
| JP | 7-258878 A | 10/1995 |
| JP | 10-59912 A | 3/1998 |
| WO | WO 2010/139755 A1 | 12/2010 |

OTHER PUBLICATIONS

English language machine translation of JP 10-59912 A published Mar. 3, 1998.
International Search Report for International Application No. PCT/EP2010/057788 dated Aug. 5, 2010.
European Search Report for Application No. 09162119 dated Sep. 7, 2009.
DE4211713 A1 English language machine-translation.
Okimoto et al., "Electrochemical Oxidation of Ketone Acylhydrazones and Their HCN Adducts in NaCN—MeOH," J. Org. Chem. 1990, pp. 1070-1076.
Mani, K.N., "Electrodialysis water splitting technology," Journal of Membrance Science, 58 (1991), pp. 117-138.
Raucq et al., "Production of sulphuric acid and caustic soda . . . ", Desalination , 91 (1993) 163-175, Elsevier Science Publishers B.V., Amsterdam, 1993.
McMurry, "Nucleophilic addition of HCN: Cyanohydrins", Organic Chemistry, Second Edition, p. 671-673, 1988.

* cited by examiner

① : sample solution
③ : electrode solution
⑥ : salt (XY) solution
⑦ : acid (HY) solution ② : aqueous solution ③ : electrode solution ④ : sample solution ⑤ : cyanide salt solution ③ : electrode solution ④ : sample solution ⑤ : cyanide salt solution ① : sample solution
② : aqueous solution
③ : electrode solution

ELECTROCHEMICAL PROCESS TO PREPARE CHEMICALS USING A CYANIDE SALT

REFERENCE TO RELATED APPLICATIONS

This application is the U.S. National Phase of PCT/EP2010/057788 filed on Jun. 3, 2010, and claims the benefit of U.S. Provisional Application No. 61/223,189, filed on Jul. 6, 2009.

The present invention relates to an electrochemical preparation process using a cyanide salt. Many syntheses are known in which hydrogen cyanide is a starting material. However, hydrogen cyanide is a highly toxic chemical and therefore the handling, storage, and transport thereof are extremely risky and preferably to be avoided.

U.S. Pat. No. 2,855,428 discloses a (so-called Singer) process to prepare amine nitriles by reacting formaldehyde and liquid hydrogen cyanide with an amine compound under acidic conditions.

DE 42 11 713 discloses a process to prepare aminodicarboxylic acid-N,N-diacetic acid compounds by reacting aminodicarboxylic acids with formaldehyde and hydrogen cyanide and hydrolyzing the formed amide and nitrile groups by addition of an acid or base to the reaction mixture.

It has now been found that the same preparation processes can also be performed using a cyanide salt, such as the alkali metal salt of cyanide, instead of hydrogen cyanide, if an electrochemical process is used that keeps the pH of the reaction mixture sufficiently low.

Accordingly, the present invention provides a process comprising the reaction of a cyanide with a hydrogen cyanide-reactive compound, characterized in that the cyanide is a cyanide salt and the process is an electrochemical process involving the transporting of a reaction mixture to which cyanide salt has been added through an electrochemical cell, in which process the cyanide salt reacts with the hydrogen cyanide-reactive compound while at least partly under the influence of an electric current the cyanide salt is acidified and the salt cation content is reduced.

Using the process of the present invention it is demonstrated that using and storing large amounts of HCN for the synthesis can be avoided. This leads to improved safety. Also, limited availability of HCN is no longer a problem. In this respect it should be noted that in many countries HCN may not be transported other than via a suitable pipeline. As an additional benefit, the compounds prepared by the electrochemical process of the present invention were found to have much lower impurity levels than comparable processes where cyanide salts are used.

It may be noted that DE 42 11 713 discloses in Example 4 the reaction of an aminodicarboxylic acid and formaldehyde with NaCN. However, during this reaction hydroxide is formed as a side product, as a result of which the reaction immediately progresses to the hydrolysis step to give the sodium salt of the carboxylic acid and, moreover, as an undesired side effect of the presence of the hydroxide ions a number of side products are formed, namely undesired derivatives or saponification products, like nitrilotriacetate (NTA), which can be avoided by the process of the present invention.

DESCRIPTION OF THE FIGURES

The following description of the invention may be more readily understood by reference to the Figures, wherein.

Figure 1:
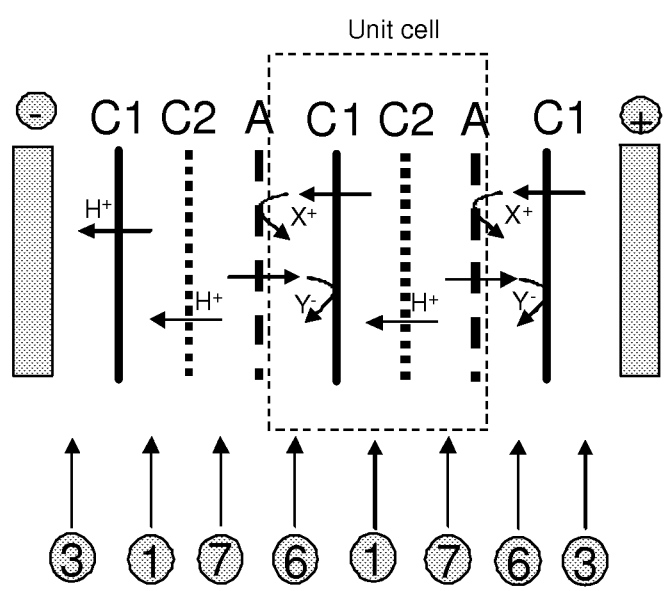
FIG. 1 illustrates a set-up for carrying out an embodiment of the invention by a process of electrodialysis wherein no salt is produced.

As indicated, the process of the invention involves a reaction mixture to which cyanide salt is added and which is transported through an electrochemical cell, in which process the cyanide salt reacts with the hydrogen cyanide-reactive compound while (at least partly) under the influence of an electric current the cyanide salt is acidified and the salt cation content is reduced. In a preferred embodiment of the process only in situ hydrogen cyanide is present, as under the process conditions the cyanide reacts instantaneously with the hydrogen cyanide-reactive compound. However, although less preferred, it is conceivable that the hydrogen cyanide is present as such for a (shortest possible) period of time before it reacts with the hydrogen cyanide-reactive compound. For example, in one embodiment the hydrogen cyanide could be transported outside the electrochemical cell to react with the hydrogen cyanide-reactive compound in a separate reactor.

The term "electrochemical process" in this application is defined as a membrane water splitting process to produce protons so as to convert water-soluble salts into their corresponding acids and bases. Or, put more simply, the electrochemical process is a process wherein the pH in several compartments of an electrochemical unit is controlled under the influence of an externally electrical potential gradient.

The electrochemical process of the invention is an electrodialysis process that uses bipolar membranes, or, an electro-electrodialysis process that uses an electrode to produce protons by electrochemical oxidation of an aqueous electrolyte combined with a cation exchange membrane to pass the protons produced into a second compartment in which the cyanide salt reacts with the hydrogen cyanide-reactive compound.

The process preferably uses bipolar ion exchange membranes in conjunction with conventional cation and/or anion exchange membranes and the separation and rearrangement of ions is effected by a direct current driving force. The absence of electrochemical transformations enables the water splitting process to be energy efficient, as well as permitting direct processing of oxidation sensitive chemicals (see also K. N. Mani, *J. Membr. Sci.*, 58, (1991), pp. 117-138).

The electrochemical process of the invention utilizes the principle that when positive and negative electrodes are put in an (aqueous) solution of an electrolyte solution and an electric potential gradient is applied thereto, oxidation and reduction reactions can take place at the anode and the cathode, respectively, leading to the transport of positive and negative ions in the solution towards their respective counter-electrodes, in particular of protons. With the arrangement of one or more ion exchange or ion-permselective or ion-semipermeable membranes between the two electrodes, the process enables transport of ionic species (such as H$^+$ ions) between different solutions, thereby separating ionic species.

It may be noted that Mitsuhiro Okimoto et al., in "Electrochemical oxidation of ketone acylhydrazones and their hydrogen cyanide adducts in sodium cyanide-methanol. Transformation of ketones to nitriles", *Journal of Organic chemistry*, Vol. 55, No. 3, 1990, pp. 1070-1076 discloses a process to electrolytically oxydate ketone acylhydrazones in methanol. In the process disclosed in this document hydrazines are electrolytically converted to hydrazones and at the same time water is electrolytically degraded to give hydrogen gas. The process disclosed in this document does not relate to a transport of ionic species between different solutions, unlike the electrochemical process of the present invention.

In the electrochemical process of the invention, the application of ion exchange membranes prevents electrochemical transformations taking place in the compartments where the hydrogen-cyanide-reactive compounds are present, which permits acidification of the reaction mixture without oxidation of chemicals that are sensitive to anodic oxidation.

The electrochemical process requires that the solution passing the electrochemical cell reasonably conducts the electric current applied. In many embodiments the starting compounds and/or products make the solution sufficiently electrically conductive. If this is not the case, it is desirable to add another compound to the solution or to other streams in the electrochemical cell to increase the conductivity thereof. This compound preferably is chosen such that it is inert and easy to separate from the intended products or can stay in the reaction product mixture (which is the case if the reaction product is itself an electrolyte and some of the intended reaction product is used to make the solution conductive). It is within the skills of the person skilled in the art to select such compounds to improve conductivity.

The solution used for the process of the present invention preferably is an aqueous solution; however, other solvents may be used as well, such as protic solvents that can be split electrochemically to produce protons by means of a bipolar membrane such as e.g. methanol or acetic acid. Mixtures of organic solvents and water are useful when one of the reactants is poorly soluble or insoluble in water.

In another embodiment the cyanide salt (also referred to as XCN in this specification) can be an alkali metal cyanide or a mixture of HCN and an alkali metal cyanide. The alkali metal cyanide preferably is sodium or potassium cyanide. The cyanide salt can also be an alkaline earth metal cyanide salt, as long as it is not insoluble in the solution used in the electrochemical cell used in the process and, preferably, the alkaline earth metal cation can pass the (cation-permeable) membranes used in the electrochemical cell used.

The hydrogen cyanide-reactive compound can be an aldehyde, such as formaldehyde or acetaldehyde; a ketone, such as acetone; an alkene, optionally substituted with further groups, such as propene nitrile; a cyanide, or an imine (Schiff's base, i.e. a reaction product of an amine and aldehyde), as also illustrated below. Preferably, the hydrogen cyanide-reactive compound is reasonably soluble in the solution used in the electrochemical cell used in the process of the invention, with reasonably soluble being defined as at least 0.1 g/l of the solution, preferably at least 1 g/l of the solution.

Depending on the selection of the hydrogen cyanide-reactive material and in some cases on the further raw materials and the reaction conditions, several embodiments of the present invention follow, which are discussed in further detail below.

Reaction equations given in this specification are only meant to illustrate several embodiments of the invention and are not always fully accurate or complete.

Aminonitrile Process

In a preferred embodiment the process of the invention is a Singer(-like) process to give aminonitriles in accordance with the equation below:

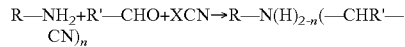

wherein n is 1 or 2. In one embodiment, R is a group selected from hydrogen, an alkyl, alkylene, alkylene amine or amino acid group, optionally substituted with one or more alkyl groups, carboxylate groups, hydroxyl groups, amino groups and/or containing one or more ether functionalities, and R' is an alkyl group optionally substituted with one or more carboxylate groups and/or a hydrogen atom; preferably, it is a hydrogen atom.

The aminonitriles formed by this Singer embodiment are suitable starting materials in the preparation of chelates, as well as for ethylene amines.

The amine can be ammonia, a primary or a secondary amine (then instead of using RNH$_2$ the reaction is started with R1R2-NH wherein each of R1 and R2 may be independently selected from the same group of compounds as R), mono-, di-, tri-, or tetra-amines or an amino acid or mixtures thereof. Preferably, the amine is an amino acid, even more preferably a naturally occurring amino acid, or an alkylamine or alkyleneamine. If in the R, R1 or R2 group another amino group is present (like in an alkyleneamine such as ethylenediamine or diethylene triamine), it should be noted that each amino group can react in the same way to give an aminonitrile.

In a particularly preferred embodiment the compound of the formula R—N(H)$_{2-n}$(—CHR'—CN)$_n$ is a glutamic acid mono- or diacetonitrile, a N-hydroxyethyl ethylenediamine mono-, di- or triacetonitrile, imino mono- or diacetonitrile (IDAN), ethylenediamine mono-, di-, tri- or tetra-acetonitrile, methylglycine mono- or diacetonitrile, hydroxyethyl amine mono- or diacetonitrile, aspartic acid mono- or diacetonitrile or a salt thereof.

These nitrile compounds can be hydrolyzed to give the corresponding amides or carboxylic acids or the salts thereof that are of use as chelating agents or precursors thereof.

It should be noted that when in the electrochemical process in accordance with the present invention wherein the cation X concentration is reduced in situ from the XCN compound, it is beneficial to have a certain buffering capacity present during the reaction. This buffering capacity ensures that the pH can be kept more readily in the range where the reaction proceeds best. In certain reactions, such as those reactions where an amino acid nitrile is formed, this buffering capacity is inherently present in the reaction mixture, making these reactions particularly preferred embodiments of this invention. It is possible to add an additional buffering compound, preferably a buffering compound that has a pKa in the pH area where the reaction between the cyanide and the hydrogen cyanide-reactive compound proceeds, and this is of particular use when no buffering capacity is present.

The pH during the process of the invention in a preferred embodiment is between 0 and 8, more preferably between 1 and 7, and most preferably between 2 and 6. While it is possible to suppress polymerization and saponification by controlling other reaction conditions at higher pH ranges, the higher pH range increases the risk that undesired polymerization reactions of cyanide compounds or saponification reactions will start to occur.

Cyanohydrin Process

In another embodiment of the process of the invention the hydrogen cyanide-reactive compound is an aldehyde or a ketone and the product formed is a cyanohydrin compound. The reaction then proceeds in accordance with the equation below:

$$R1R2\text{-}C=O+XCN \rightarrow R1R2\text{-}C(OH)CN$$

The cyanohydrin formed is a suitable starting material in the formation of methyl methacrylates or other acrylates. When the process of the present invention is used for the formation of cyanohydrins, it is also possible to make glyconitrile, which is a known compound for storing an excess of hydrogen cyanide (as glyconitrile is less volatile than HCN, less susceptible to polymerization, and therefore less dangerous). Besides, in a number of chemical reactions glyconitrile can be used as raw material instead of HCN. Alternatively, using this route acetone cyanohydrin can be made, which is also known to be a HCN source in certain chemical syntheses.

Hydantoin Process

In another embodiment of the process of the invention the hydrogen-reactive compound is also an aldehyde or a ketone, but the reaction is performed in the presence of ammonia and carbon dioxide to give hydantoin as the product. The reaction then proceeds in accordance with the equation below:

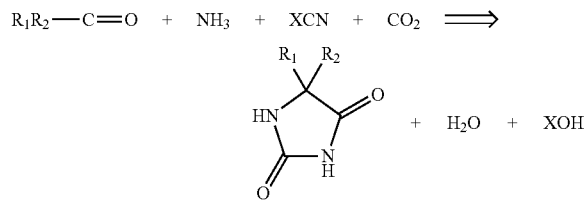

The cyclic hydantoin compound is a suitable starting material in the production of amino acids such as methionine and phenylglycine, which are suitably applied in the animal feed and foodstuff industries.

Addition Process

In another embodiment of the process of the invention the hydrogen cyanide-reactive compound is an unsaturated hydrocarbon compound and the process is a Michael addition reaction, for example in accordance with the equation below:

$$XCN+CH_2=CH\text{-}CN \rightarrow NC\text{-}CH_2\text{-}CH_2\text{-}CN$$

The dinitrile formed is the raw material for the formation of 1,4-diaminobutane, which is used for the synthesis of nylons. Another addition reaction of commercial interest is that in accordance with the equation below:

$$CH_2=CH\text{-}CH=CH_2+2XCN \rightarrow NC\text{-}CH_2\text{-}CH_2\text{-}CH_2\text{-}CH_2\text{-}CN$$

The adiponitrile formed is a starting material for nylon 66.

Cyanide Coupling Process

In yet another embodiment of the process of the invention the hydrogen cyanide-reactive compound is the cyanide itself, to give dicyan (also called cyanogen).

$$2XCN \rightarrow NC\text{-}CN$$

Dicyan is a suitable starting material in the preparation of oxalic acid derivatives.

It should be understood that where in the above reactions the reaction of hydrogen cyanide with the hydrogen cyanide-reactive compound is known to proceed only under certain conditions, such as only at an elevated temperature, elevated pressure, or in the presence of a catalyst, these conditions may also need to be applied when performing the same reaction with a cyanide salt under electrochemical conditions in accordance with the present invention. In this respect it is known for example that the preparation of adiponitrile by reacting 1,3-butadiene with hydrogen cyanide is performed in the presence of a catalyst and that the coupling of cyanides to give dicyan normally is also performed in the presence of a catalyst.

The membranes of the electrochemical unit applied should be able to withstand the reaction conditions needed/used for the reaction and the chemicals present in the reaction mixture, which means that for certain reactions there is no absolute freedom in selecting the membranes. It is within the skills of a person skilled in the art to select the most appropriate membrane for each specific reaction.

Though it is safest to fully control the pH by the electrochemical process, it should be understood that complete or partial chemical acidification of the cyanide salt is also possible. Thus, in one embodiment the pH during the process can be kept completely or in part in the above-mentioned preferred range by the addition of an organic or inorganic acid or the use of an acidic ion exchange resin. This may lead to a more cost efficient process as in some embodiments a chemical acidification is preferred from an energy consumption point of view. However, the use of a cyanide salt and pH control by adding an organic or inorganic acid may give rise to the formation of inorganic or organic salt containing the cation derived from the cyanide salt used and the anion of the acid used. In a preferred embodiment this disadvantage can be avoided by using any of the starting materials or products as the acid to acidify to the sufficiently low pH (such as the chelating agent in the acid form, which is the intended end product of the amino acid nitrile route described above). If chemical acidification is applied, separation of the inorganic or organic salt formed may be needed and this can be conducted using conventional techniques such as crystallization, electrodialysis, ion-exchange resins, and membrane filtration (such as nanofiltration).

In a preferred embodiment the process is performed in such a way that when a salt is made as a by-product of chemical acidification, this salt is made in a compartment separated from the compartment containing the produced hydrogen cyanide and the cyanide-reactive component. This avoids the potential need for an additional salt separation step. This can be conducted in principle by using an electrodialysis process containing monopolar membranes.

To be able to use the process of the invention and partially acidify by chemical acidification instead of carrying out the full pH control by the electrochemical process and to still make a salt-free product from this reaction mixture, an additional separation step may be used. Also in this case, conventional separation techniques may be applied such as crystallization, electrodialysis, ion-exchange resins, and membrane filtration (such as nanofiltration). In a further preferred embodiment, this separation can be avoided by using an electrodialysis process, having a set-up wherein no salt is produced. An example of such a set-up is shown in FIG. 1, where a first solution containing the cyanide salt and a hydrogen cyanide-reactive component (referred to as sample solution 1 in FIG. 1) is fed to a first compartment that is separated by a cation-permeable membrane (C2) at the anode side and by a cation-permeable membrane (C1) at the cathode side, a second solution containing an inorganic or an organic acid (referred to as acid (HY) solution 7 in FIG. 1) is fed to a second compartment of said electrodialysis set-up on the anode side of said cation-permeable membrane (C2), and a third solution of an electrolyte (referred to as salt (XY) solution 6 in FIG. 1), preferably containing anions of the organic or inorganic acid (Y) and cations (X) of the cyanide salt, is fed to a third compartment on the cathode side of said cation-permeable membrane (C1) of said electrodialysis set-up.

The term "cation-permeable membrane" as used in this application means a functional membrane through which cations are permeable and anions are hardly permeable or impermeable. For the membrane, use can advantageously be made of a membrane which contains sulfonic acid groups, carboxylic acid groups, and other groups which will have a negative charge when dissociated, which membrane in many cases is composed of a styrenic polymeric homogenous membrane. Commercially available membranes include, for instance, Selemion CMV (manufactured by Asahi Glass Co., Ltd.), Aciplex CK-1, CK-2, K-101, and K-102 (manufactured by Asahi Chemical Industry Co., Ltd.), Neosepta CL-25T, CH-45T, C66-5T, and CHS-45T (manufactured by Tokuyama Corporation), Nafion 120, 315, and 415 (manufactured by Du Pont Company), and Fumasep FTCM, FKB, and FKL (manufactured by FuMA-Tech GmbH). The membrane can be chosen according to the species of alkali metal salt or according to other components that may be present in the solutions on either side of the membrane that might for instance harm or reduce the lifetime of the membranes.

The term "anion-permeable membrane" as used in this application means a functional membrane through which anions are permeable and cations are hardly permeable or impermeable. For the membrane, use can advantageously be made of a membrane which contains quaternary amine groups and other groups which will have a positive charge when dissociated, and which may be composed of a styrenic polymeric homogenous membrane. Commercially available membranes include, for instance, Selemion AMV (manufactured by Asahi Glass Co., Ltd.), Aciplex A201, A192, and A501SB (manufactured by Asahi Chemical Industry Co., Ltd.), Neosepta AMX, AHA, and ACM (manufactured by Tokuyama Corporation), and Fumasep FAA, FAP, and FTAM (manufactured by FuMA-Tech GmbH). The membrane can be chosen according to the process conditions or according to the components that may be present in the solutions on either side of the membrane that might for instance harm or reduce the lifetime of the membranes.

Bipolar Membrane Electrodialysis

Bipolar membrane electrodialysis (BPM), which is basically a special form of electrodialysis using a hydrogen ion-permselective membrane, is the most advantageous electrodialysis process. This is because when using other electrodialysis methods than BPM electrodialysis—i.e. those based on the use of anion- and cation-permeable membranes only—still a mineral or organic acid is required and the by-product normally is a salt, which may be considered a waste stream. In a BPM electrodialysis process it is possible to produce an alkaline product as a by-product, which is a side stream that is of value, for example because it can be used in the hydrolysis of the aminonitrile or the amide from the said aminonitrile process to produce the corresponding amino (poly)carboxylate.

FIG. 1 shows the embodiment of a preferred electrodialysis process, wherein the acid-derived proton is transported to a compartment on the cathode side through the cation-permeable membrane (C2) and wherein the anion (Y) of the acid (HY) used is transported to a compartment on the anode side through the anion-permeable membrane (A), and wherein the cyanide salt-derived cation (X) is transported to the same compartment as the acid-derived anion, separate from the compartment in which the hydrogen cyanide-reactive compound is reacted, to give the desired reaction product and a separate salt stream (6).

Figure 2:
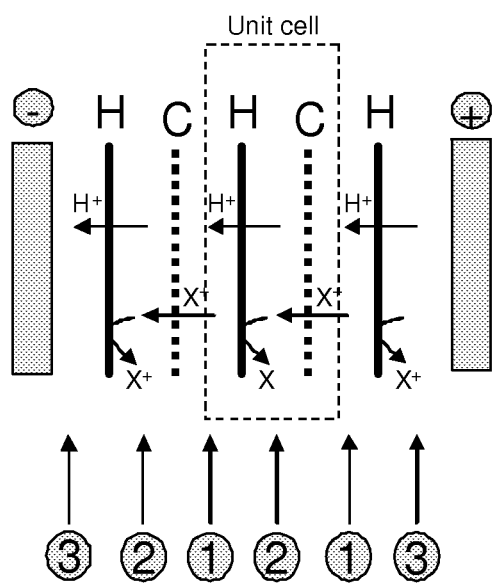
FIG. 2 illustrates an embodiment of the invention wherein electrodialysis is performed with a hydrogen ion-permselective membrane on the anode side and a cation-permeable membrane on the cathode side.

In another preferred embodiment the electrodialysis is performed with a hydrogen ion-permselective membrane on the anode side and a cation-permeable membrane on the cathode side. According to the electrodialysis to be used in the production process as shown in FIG. 2, each membrane cell through which an aqueous solution of a cyanide salt and optionally the hydrogen cyanide-reactive compound (referred to as sample solution 1 in FIG. 2) passes, comprises a hydrogen ion-permselective membrane H as a semipermeable membrane on the anode side and a cation-permeable membrane C as an ion-exchange membrane on the cathode side. An aqueous solution 2 is fed on the anode side of the hydrogen ion-permselective membrane H and the cathode side of the cation-permeable membrane C. In this procedure, alkali metal ions in the aqueous solution 1 move towards the cathode and permeate through the cation-permeable membrane C and migrate into the aqueous solution 2. In effect, hydrogen ions migrate separately from the aqueous solution 2 on the anode side of the hydrogen ion-permselective membrane H through the hydrogen ion-permselective membrane H to the aqueous sample solution 1. By this mechanism, alkali metal ions in the aqueous sample solution 1 are replaced with hydrogen ions to reduce the number of alkali metal ions in the aqueous sample solution 1.

The term "hydrogen ion-permselective membrane" as used in this application means a functional membrane through which only hydrogen ions are permeable and other cations or anions are impermeable, and which is a hybrid membrane composed of laminated cation-exchange membrane and anion-exchange membrane. When an electric potential gradient is applied to the membrane, water is decomposed to form hydrogen ions and hydroxide ions, and the hydrogen ions and hydroxide ions move towards the cathode side and the anode side, respectively, and the hydroxide ions react with hydrogen ions in the aqueous solution 2 to form water or to make the aqueous solution (more) alkaline. Thus, only hydrogen ions can apparently permeate through the membrane. As examples of commercially available hydrogen ion-permselective membranes may be mentioned Selemion HSV (manufactured by Asahi Glass Co., Ltd.), Neosepta BP1E (manufactured by Tokuyama Corporation), and Fumasep FBM (manufactured by FuMA-Tech GmbH).

The aqueous solution 2 may be an aqueous acidic solution, an aqueous alkaline solution or a neutral aqueous solution with sufficient electric conductivity to enable an electric current to be passed through the solution. The electric conductivity of the aqueous solution 2 should be between 1 and 500 mS/cm, preferably between 20 and 400 mS/cm, and more preferably between 50 and 300 mS/cm. In a preferred embodiment the aqueous solution 2 is a hydroxide solution of the alkali metal ion from the cyanide salt.

The aqueous solution 2 can be replaced during the electrodialysis in continuous or batch operation, because during the process the concentration of ionic components in the solution 2 may increase such that very high conductivities are achieved, which may cause deterioration of the current efficiency. The aqueous solution 2 may be circulated and recycled.

The aqueous solution 2 may contain an acid, base or salt, preferably a base, the concentration of the aqueous acid, base or salt solution in one embodiment falling in the range from 1 to 20 wt %.

As an electrode solution 3 to be circulated in electrode cells, an alkaline, acidic or neutral solution may be used, as long as it sufficiently conducts the electric current needed and does not cause the electrodes to deteriorate. In one embodiment the solution 3 may be a solution of an acid, base or salt in a concentration of between 0.5 and 10 wt %, preferably between 1 and 5 wt %, most preferably 2 to 5 wt %. If a basic solution is used, a base identical to the aqueous solution 2 for the electrodialysis is preferably employed. If the concentration of the electrode solution is too high, electrode plates may be corroded faster. On the other hand, if the concentration is too low, the electrical resistance may be high, leading to excessive energy consumption.

Figure 3:
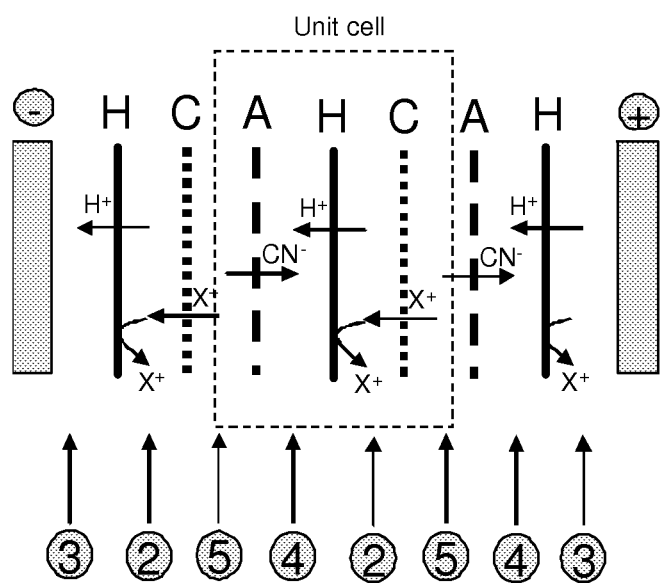
FIG. 3 illustrates an embodiment of the invention wherein electrodialysis is performed in a 3-compartment configuration in which each unit cell consists of a hydrogen ion-permselective membrane, a cation-permeable membrane, and an anion-permselective membrane and three different fluid compartments.

In another embodiment the electrodialysis is performed in a 3-compartment configuration in which each unit cell consist of a hydrogen ion-permselective membrane, a cation-permeable membrane, and an anion-permselective membrane and three different fluid compartments. According to the electrodialysis to be used in the production process as shown in FIG. 3, each membrane cell through which an aqueous solution passes, optionally in combination with the hydrogen cyanide-reactive compound (referred to as sample solution 4 in FIG. 3), comprises a hydrogen ion-permselective membrane H as a semipermeable membrane on the anode side and an anion-permeable membrane A as an ion-exchange membrane on the cathode side. An aqueous solution 2 is fed on the anode side of the hydrogen ion-permselective membrane H and the cathode side of the cation-permeable membrane C. A cyanide salt solution 5 is fed on the anode side of the cation-permselective membrane C and the cathode side of the anion-permeable membrane A. In this procedure, alkali metal ions in the cyanide salt solution 5 move towards the cathode and permeate through the cation-permeable membrane C and migrate into the aqueous solution 2. Cyanide ions in the solution 5 move towards the anode and permeate through the anion-permeable membrane A and migrate into the sample solution 4. In effect, hydrogen ions migrate separately from the aqueous solution 2 on the anode side of the hydrogen ion-permselective membrane H through the hydrogen ion-permselective membrane H to the sample solution 4. By this mechanism, cyanide salt solution 5 is split into two separate streams: an acidic sample solution 4 and a basic alkali metal ion-containing aqueous solution 2.

In all embodiments, the applied electric power in the electrodialysis is preferably controlled either by a constant voltage method or by a constant current method. At increased current density, the required treatment time decreases. However, increased current density requires increased voltage and therefore the electric power input increases. This results in a temperature increase in the solution generated by the ohmic resistance in the electrodialysis unit. Accordingly, the upper limit of both potential and current is preferably controlled so as to maintain the temperature of the solution within such a range as will not cause deterioration of the membranes and of the starting materials or reaction products.

The electrodialysis operation is generally performed in a semi-batch system in which the cyanide salt solution is added to the hydrogen cyanide-reactive component with the pH being maintained within a predetermined range, and the sample solution is exchanged after completion of each dialysis operation. However, the aqueous solution 2 does not need to be exchanged at the same time and can be used well into a next batch operation, when it is replaced with a new portion of the aqueous solution. By this operation, the concentration of alkali metal ions in the aqueous solution of cyanide salt can be reduced efficiently. The electrodialysis can also be performed in continuous operation, for instance by a feed and bleed operation involving continuous addition of the cyanide salt and the hydrogen cyanide-reactive compounds and removal of the reaction mixture or part of the reaction mixture, while simultaneously alkali metal ions are removed and hydrogen ions are produced in the acidic cyanide solution by means of the process of the present invention.

In the batch treatment, the completion of the electrodialysis operation should be determined when dosing of the cyanide solution is completed and/or when the pH value of the aqueous sample solution reaches a predetermined value. When the electrodialysis is performed in order to form a cyanide salt solution from which alkali metal ions are removed, the electrodialysis operation should preferably be completed at the time when the concentration of alkali metal ions reaches the lower permissible limit or sooner. This is because excessive electrodialysis for the purpose of complete removal of the alkali metal ions will cause the current efficiency to deteriorate and increase the amount of acid ions and bases migrating and contaminating the cyanide salt solution.

Figure 4:
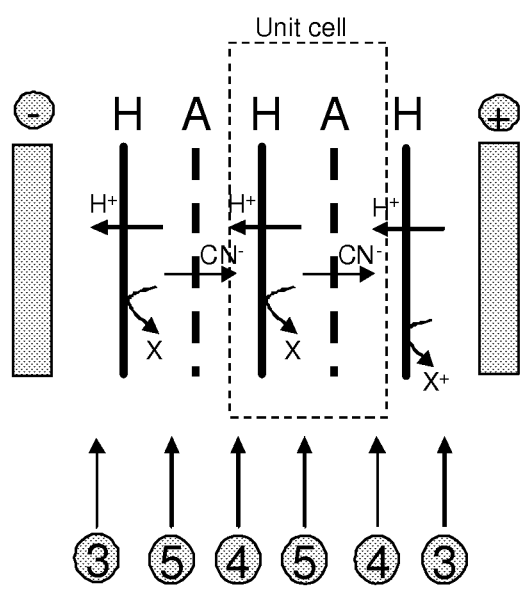
FIG. 4 illustrates an embodiment of the invention wherein electrodialysis is performed with a hydrogen ion-permselective membrane on the anode side and an anion-permeable membrane on the cathode side.

In one embodiment, the electrodialysis is performed with a hydrogen ion-permselective membrane on the anode side and an anion-permeable membrane on the cathode side. According to the electrodialysis to be used in the production process as shown in FIG. 4, each membrane cell through which an aqueous neutral to acidic solution optionally containing the hydrogen cyanide-reactive compound (referred to as sample solution 4 in FIG. 4) passes, comprises a hydrogen ion-permselective membrane H as a semipermeable membrane on the anode side and an anion-permeable membrane A as an ion-exchange membrane on the cathode side. An aqueous cyanide salt solution 5 is fed on the anode side of the hydrogen ion-permselective membrane H and the cathode side of the anion-permeable membrane A. In this procedure, hydrogen cyanide is produced in the sample solution 4. In effect, hydrogen ions migrate separately from the cyanide salt solution 5 on the anode side of the hydrogen ion-permselective membrane H through the hydrogen ion-permselective membrane H to the sample solution 4. By this mechanism, the basicity of the cyanide salt solution 5 increases and the cyanide content decreases, while hydrogen cyanide is produced in the sample solution 4.

EXAMPLES

Figure 5:
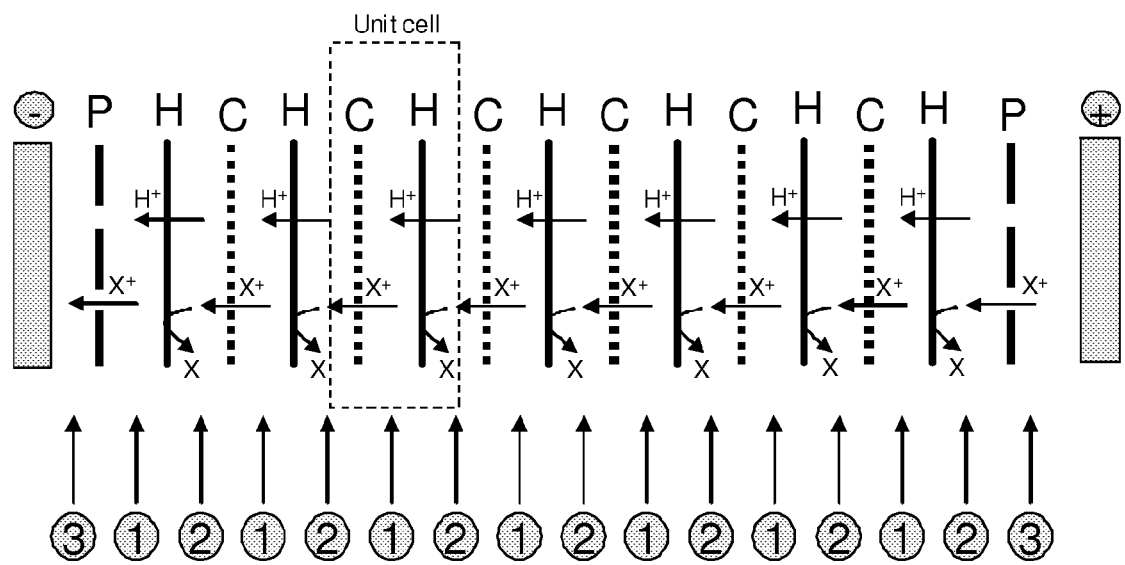
FIG. 5 illustrates a two-compartment bipolar membrane electrodialysis configuration containing seven hydrogen ion-permselective membranes, six cation-permeable membranes, an anode and a cathode.

The electrochemical stack of cells used in the Examples was a so-called two-compartment bipolar membrane electrodialysis configuration according to FIG. 5 containing seven hydrogen ion-permselective membranes H (type BP1-E obtained from Eurodia), six cation-permeable membranes C (type CMB obtained from Eurodia), two cation-permeable membranes P (type C66-10F obtained from Eurodia), and two electrodes (anode and cathode) both made of nickel. In both the anode and the cathode compartment a 5 wt % NaOH solution (referred to as electrode solution 3 in FIG. 5) was circulated from a single 2-liter vessel using two pumps through the anode and the cathode compartment. Oxygen and hydrogen gas evolving from the electrodes were diluted with excess of air and separated from the vessel. The electrode solutions were constant in concentration throughout the trials in the Examples. At the anode side of each hydrogen ion-permeable membrane H initially a 2 wt % NaOH solution was circulated (aqueous solution 2, FIG. 5) from a 1-liter vessel. During the trials, the caustic concentration increased and when the concentration reached about 8 wt % (based on a measured electric conductivity of about 270 mS/cm), part of the caustic was removed and fresh deionized water added to restart at low concentration (about 150 mS/cm). At the cathode side of each hydrogen ion-permselective membrane H a solution containing the hydrogen cyanide-reactive component (sample solution 1, FIG. 5) was circulated from a 1-liter reactor vessel as further indicated below.

Example 1

The Preparation of Glycolonitrile

A 1-liter reactor vessel equipped with a stirrer, a condensor, and a pH electrode was precharged with 900 grams of water containing 30 grams of trisodium citrate and 10 grams of citric acid.

This solution was circulated by means of a centrifugal pump through the electrodialysis stack along the cathode side of each hydrogen ion-selective membrane (sample solution 1, FIG. 5). During a period of 170 minutes, 476 grams of a 43.9 wt % formaldehyde solution (7 moles) and 1,189 grams of a 28.7 wt % sodium cyanide solution (7 moles) were simultaneously dosed into the reactor and at the same time the acidity of the reaction mixture was maintained at pH=4 by adjusting the electric current applied through the electrodialysis stack. At the end of the dosing, the circulation and the electric current through the electrodialysis stack were continued for 5 minutes to obtain a pH of 3. The circulation and the electric current were stopped, and the reaction mixture was collected.

$^1$H-NMR analysis of the reaction mixture showed that the main component was glycolonitrile.

Example 2

A—the Preparation of Glutamic Acid N,N-Dinitrile (GLDN)

A 1-liter reactor was charged with 842.5 grams of a 40 wt % MonoSodium-Glutamate (MSG) solution (2 moles), and at room temperature 136.8 grams of a 43.3 wt % formaldehyde solution (2 moles) were added and mixed. The contents of the reactor were then circulated over the electrodialysis stack along the cathode side of each hydrogen ion-selective membrane (sample solution 1, FIG. 5), and a current was applied to the electrodialysis stack in order to maintain an acidity of pH=4. Simultaneously, constant dosing of a 28.8 wt % sodium cyanide solution was started at a dosing rate of 679.4 grams (4 moles of NaCN) in 180 minutes while keeping the pH constant at about 4 by adjusting the current. Circa 90 minutes after the start of the cyanide dosing, a 43.3 wt % formaldehyde solution was dosed at a rate of 136.8 grams (2 moles) in 90 minutes. At the end of the cyanide/formaldehyde dosing, the electrodialysis process was stopped and product from the reactor and the electrodialysis system was collected and saponified as described below.

B—Saponification of the GLDN to Give Glutamic Acid N,N-Diacetic Acid Tetrasodium Salt (GLDA-Na4)

A 1-liter stainless steel reactor equipped with a heating bath, a Dean-Stark set-up, and a propeller-type impeller was precharged with 200 grams of a 25 wt % NaOH solution (1.25 moles). The reactor content was heated to boiling. An amount of MSG corresponding to 1.3 moles of MSG collected from the product mixture of Example 2A was added in 90 minutes. Simultaneously dosing started of 240 grams of a 50 wt % NaOH solution (3 moles). Dosing time of the caustic was 60 minutes.

During the complete reaction the mixture was boiling. Water was dosed slowly to the reaction mixture when the boiling point exceeded 110° C. After dosing was completed, ammonia was distilled off for 130 minutes. The reactor content was cooled to room temperature and collected. An overall yield of 84% of the initially charged MSG was achieved.

The invention claimed is:
1. Process comprising the reaction of a cyanide with a hydrogen cyanide-reactive compound, wherein the cyanide is a cyanide salt and the process is an electrochemical process involving the feeding of a reaction mixture to which cyanide salt has been added into an electrochemical cell, in which process the cyanide salt reacts with the hydrogen cyanide-reactive compound, while at least partly under the influence of an electric current the cyanide salt is acidified and the salt cation content is reduced, and wherein the electrochemical process is a membrane water splitting process to produce protons so as to convert water soluble salts into their corresponding acids and bases.

2. The process of claim 1 wherein the electrochemical cell is a bipolar membrane electrodialysis cell.

3. The process of claim 2 wherein the bipolar membrane electrodialysis cell contains bipolar membranes and cation-permeable membranes.

4. The process of claim 2, wherein only in situ hydrogen cyanide is present, wherein under process conditions the cyanide reacts instantaneously with the hydrogen cyanide-reactive compound.

5. The process of claim 2, wherein the acidified cyanide salt is present as such for a period of time before it reacts with the hydrogen cyanide-reactive compound in a separate reactor.

6. The process of claim 2, wherein the hydrogen cyanide-reactive material is an imine-functional condensation product of an amine and aldehyde or ketone, and the product is an aminonitrile.

7. The process of claim 6, containing an additional step wherein the nitrile is hydrolyzed to a carboxylic acid, an amide or a carboxylate salt.

8. The process of claim 2, wherein the cyanide salt is an alkali metal cyanide or a mixture of HCN and an alkali metal cyanide.

9. The process of claim 8, wherein the alkali metal cyanide is sodium cyanide or potassium cyanide.

10. The process of claim 1, wherein only in situ hydrogen cyanide is present, wherein under process conditions the cyanide reacts instantaneously with the hydrogen cyanide-reactive compound.

11. The process of claim 1, wherein the acidified cyanide salt is present as such for a period of time before it reacts with the hydrogen cyanide-reactive compound in a separate reactor.

12. The process of claim 1, wherein the hydrogen cyanide-reactive material is an imine-functional condensation product of an amine and aldehyde or ketone, and the product is an aminonitrile.

13. The process of claim 12 wherein the hydrogen cyanide-reactive material is an imine-functional condensation product of an amino acid and aldehyde or ketone, and the product is an amino acid nitrile.

14. The process of claim 13 containing an additional step wherein the nitrile is hydrolyzed to a carboxylic acid, an amide, or a carboxylate salt.

15. The process of claim 12 containing an additional step wherein the nitrile is hydrolyzed to a carboxylic acid, an amide or a carboxylate salt.

16. The process of claim 1, wherein the solution in which the process is carried out is an aqueous solution, a solution of organic protic solvents, or a mixture of organic solvents and water.

17. The process of claim 1, wherein the cyanide salt is an alkali metal cyanide or a mixture of HCN and an alkali metal cyanide.

18. The process of claim 17, wherein the alkali metal cyanide is sodium cyanide or potassium cyanide.

* * * * *

UNITED STATES PATENT AND TRADEMARK OFFICE
CERTIFICATE OF CORRECTION

PATENT NO. : 8,956,520 B2  
APPLICATION NO. : 13/322702  
DATED : February 17, 2015  
INVENTOR(S) : Wilhelmus Joannes Theodorus Maria Appelman et al.

Page 1 of 2

It is certified that error appears in the above-identified patent and that said Letters Patent is hereby corrected as shown below:

In the Claims

Claim 4, Column 12, Line 30, delete "2" and insert -- 1 --.

Claim 5, Column 12, Line 34, delete "2" and insert -- 1 --.

Claim 6, Column 12, Line 37, delete "2" and insert -- 1 --.

Claim 7, Column 12, Line 41 - 43, replace with the following:

-- The process of claim 6 wherein the hydrogen cyanide-reactive material is an imine-functional condensation product of an amino acid and aldehyde or ketone, and the product is an aminoacid nitrile --.

Claim 8, Column 12, Line 44 - 46, replace with the following:

-- The process of claim 6 containing an additional step wherein the nitrile is hydrolyzed to a carboxylic acid, an amide or a carboxylate salt --.

Claim 9, Column 12, Line 47 - 48, replace with the following:

-- The process of claim 7 containing an additional step wherein the nitrile is hydrolyzed to a carboxylic acid, an amide, or a carboxylate salt --.

Claim 10, Column 12, Line 49 - 52, replace with the following:

-- The process of claim 1, wherein the solution in which the process is carried out is an aqueous solution, a solution of organic protic solvents, or a mixture of organic solvents and water --.

Claim 11, Column 12, Line 53 - 56, replace with the following:

-- The process of claim 1, wherein the cyanide salt is an alkali metal cyanide or a mixture of HCN and an alkali metal cyanide --.

Signed and Sealed this  
Fourteenth Day of July, 2015

Michelle K. Lee  
*Director of the United States Patent and Trademark Office*

CERTIFICATE OF CORRECTION (continued)
U.S. Pat. No. 8,956,520 B2

In the Claims

Claim 12, Column 12, Line 57 - 60, replace with the following:

-- The process of claim 11, wherein the alkali metal cyanide is sodium cyanide or potassium cyanide --.

Claim 13, Column 12, Line 61 - 64, replace with the following:

-- The process of claim 2, wherein only in situ hydrogen cyanide is present, wherein under process conditions the cyanide reacts instantaneously with the hydrogen cyanide-reactive compound --.

Claim 14, Column 12, Line 65 - 67, replace with the following:

-- The process of claim 2, wherein the acidified cyanide salt is present as such for a period of time before it reacts with the hydrogen cyanide-reactive compound in a separate reactor --.

Claim 15, Column 13, Line 1 - 3, replace with the following:

-- The process of claim 2, wherein the hydrogen cyanide-reactive material is an imine-functional condensation product of an amine and aldehyde or ketone, and the product is an aminonitrile --.

Claim 16, Column 13, Line 4 - 7, replace with the following:

-- The process of claim 15, containing an additional step wherein the nitrile is hydrolyzed to a carboxylic acid, an amide or a carboxylate salt --.

Claim 17, Column 13, Line 8 - 10, replace with the following:

-- The process of claim 2, wherein the cyanide salt is an alkali metal cyanide or a mixture of HCN and an alkali metal cyanide --.

Claim 18, Column 13, Line 11 - 12, replace with the following:

-- The process of claim 17, wherein the alkali metal cyanide is sodium cyanide or potassium cyanide --.